United States Patent [19]
Bender et al.

[11] 3,978,225

[45] Aug. 31, 1976

[54] HETEROCYCLIC HOMOPROSTANOIDAL DERIVATIVES

[75] Inventors: Allan D. Bender, Swarthmore; Charles E. Berkoff, Huntingdon Valley; William G. Groves, Blue Bell, all of Pa.

[73] Assignee: SmithKline Corporation, Philadelphia, Pa.

[22] Filed: May 13, 1975

[21] Appl. No.: 577,136

[52] U.S. Cl. ............................ 424/276; 260/327 H; 260/327 M; 260/340.9; 424/277; 424/278
[51] Int. Cl.$^2$............... C07D 317/26; C07D 327/10; C07D 339/06; C07D 341/00
[58] Field of Search ........ 260/327 M, 327 H, 340.9; 424/276, 277, 278

[56] References Cited
OTHER PUBLICATIONS

Kuranova et al., J. Org. Chem., (USSR) 1973, 9(5); 946–952.

Asselineau et al., Bull. Soc. Chim., France, 1955: 1241–1244.

Kaufmann et al., Chem. Ber., 92: 2789–2797 (1959) [cited as C.A. 54: 5453–5455].

Wood, Lipids 2(3), 199–203 (1967) [cited as C.A. 67: 45073a].

*Primary Examiner*—Natalie Trousof
*Assistant Examiner*—Cecilia M. S. Jaisle
*Attorney, Agent, or Firm*—Joseph A. Marlino; Richard D. Foggio; William H. Edgerton

[57] ABSTRACT

Heterocyclic homoprostanoidal derivatives are prepared. These compounds have valuable antiprostaglandin activity specifically inhibiting prostaglandin synthesis and antagonizing diarrhea induced by prostaglandin $E_2$ ($PGE_2$).

5 Claims, No Drawings

HETEROCYCLIC HOMOPROSTANOIDAL DERIVATIVES

This invention relates to novel homoprostanoidal derivatives having valuable antiprostaglandin activity. More specifically, the compounds of this invention inhibit prostaglandin synthesis and antagonize diarrhea induced by $PGE_2$.

There have been strong indications that the antiinflammatory activity of non-steroidal compounds such as aspirin, indomethacin, and phenylbutazone was due to their ability to inhibit the synthesis of prostaglandins (Nature New Biology, Vol. 231, June 23, 1971). The inhibition of prostaglandin synthesis is considered by many skilled in the art to perhaps be the mechanism underlying other therapeutic actions of aspirin and indomethacin like compounds.

It is therefore the object of the present invention to provide novel homoprostanoidal derivatives which display the above mentioned prostaglandin antagonism and which may lend themselves as anti-inflammatory agents.

The compounds of this invention are represented by the following structural formula:

Formula 1

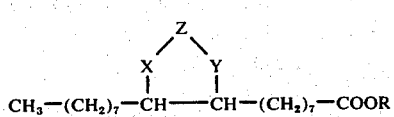

in which:

R represents hydrogen or lower alkyl of from 1–3 carbon atoms;

X and Y being the same represent oxygen or sulfur; and

Z represents sulfoxide (S=O), thioxo (C=S) or methylene ($CH_2$).

Advantageous compounds of this invention are represented by the above structural formula when R represents methyl, X and Y represent oxygen, and Z represents sulfoxide.

Plastic compositions containing the carbonato esters, i.e., where X and Y represent oxygen and Z represents C=O are disclosed in U.S. Pat. No. 2,858,286. There is no biological activity disclosed in the patent.

The compounds of this invention may be used in the form of metallic salts, such as, for example, alkali metal or ammonium salts.

The compounds of Formula 1 are prepared according to the following sequence of reactions:

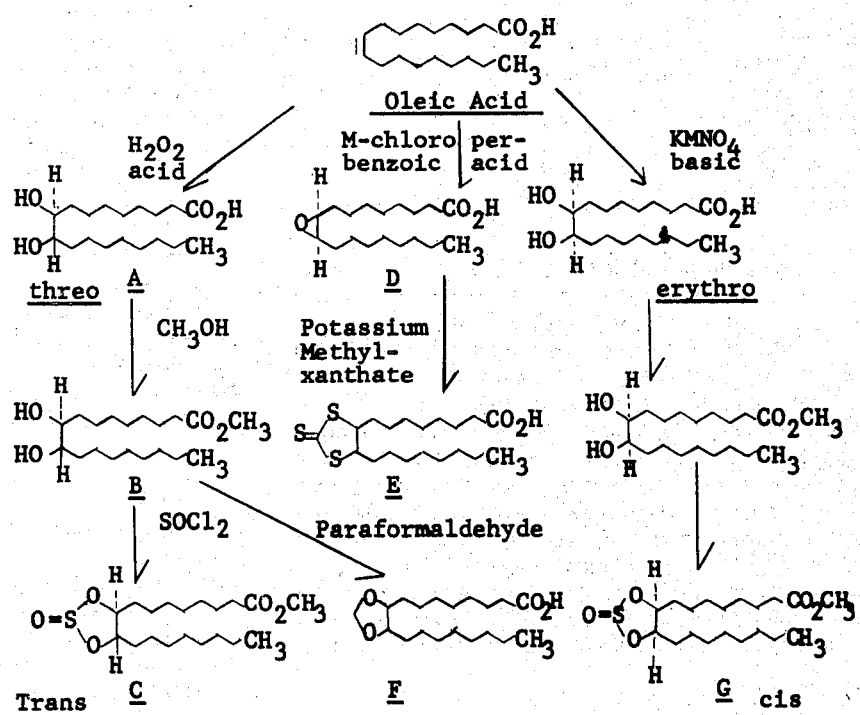

These reactions are carried out using readily available starting materials and give excellent yields of the end product. Oleic acid yields two isomeric 9,10-dihydroxystearic acids depending on the mode of synthesis, J. Chem. Soc. 1828, 1926. The erythro isomer results from the treatment of oleic acid with basic permanganate. The threo isomer, Compound A, is readily obtained when oleic acid is oxidized using hydrogen peroxide under acidic conditions. The threo ester, Compound B, is chosen for conversion to the heterocycle, Compound C, because the resulting compound bears a trans configuration of the ring hydrogen atoms and thus corresponds to the natural prostaglandins. Unless otherwise specified in the description and accompanying claims, it is intended to include all isomers whether separated or mixtures thereof.

Oleic acid is transformed to the cis epoxide, Compound D, by employing m-chloroperbenzoic acid (J. Amer. Chem. Soc., 66, 1925, 1944) and further reaction with potassium methylxanthate yields the trans dithia acid of Compound E.

The methyl ester B can be reacted with thionyl chloride to yield the heterocycle C. Alternatively ester B can be reacted with paraformaldehyde to yield the dioxa Compound F. Similarly, the erythro acid is converted via the methyl ester to the cis heterocycle, Compound G.

The compounds of this invention have been demonstrated to inhibit prostaglandin synthesis and antagonize diarrhea induced by $PGE_2$ by employing modified standard test procedures. The prostaglandin synthesis inhibition method as employed is reported by Takeguchi and Sih, *Prastaglandins*, 2, 169, 1972. The principle entails the arachidonic acid-dependent formation of adrenochrome from L-epinephrine during prostaglandin biosynthesis. Indomethacin, phenylbutazone and aspirin were used as reference compounds. The results of this test are set forth below in Table 1.

Table 1

| Inhibition of Prostaglandin Synthesis | |
|---|---|
| Compound | $ID_{50}$ |
| Indomethacin | 2 $\mu M$ |
| Phenylbutazone | 875 $\mu M$ |
| Aspirin | 3700 $\mu M$ |
| Compound E | 390 $\mu M$ |
| Compound F | 1000 $\mu M$ = 30% Inhibition |
| Compound C | 1000 $\mu M$ = 20% Inhibition |

The antagonism of diarrhea induced by prostaglandin $E_2$ ($PGE_2$) was determined by employing the modified standard animal pharmacological test procedure as reported in *Intra Science Chem. Rept* 6:1-9, 1972 and *Annals of the New York Academy of Sciences* 180:386-95, 1971. Briefly the test comprises administering the test compounds subcutaneously 15 minutes prior to an intraperitoneal injection of $PGE_2$. Each animal is examined for diarrhea (which results after the administration of $PGE_2$) every 15 minutes for one hour post-drug. Polyphloretin phosphate and 7 oxa-13-prostynoic acid, both well known antagonists of prostaglandin induced diarrhea, were employed as reference compounds. Results of tests conducted for the inhibition of $PGE_2$ diarrhea in mice are disclosed in Table 2.

Table 2

| Inhibition of $PGE_2$ Diarrhea in Mice | | | | | | | |
|---|---|---|---|---|---|---|---|
| | | Percent Change, Diarrhea Incidence | | | | | |
| Compound | Dose mg/kg S.C. | 80 | 40 | 20 | 10 | 5 | 1 | 0.2 |
| PPP* | | −68 | −65 | −36 | −26 | −4 | | |
| 7-oxa-13-prostynoic acid | | | | | | −100 | −100 | −15 |
| G | | | 0 | −57 | −29 | −14 | | |
| F | | | −14 | 0 | −36 | 0 | | |
| C | | | −8 | −54 | −31 | +15 | | |

*polyphloretin phosphate

These results clearly indicate that the compounds of this invention demonstrate antidiarrheal effects in these tests.

The novel compounds of this invention may be administered orally or parenterally to an animal in conventional dosage unit forms such as tablets, capsules, injectables or the like by incorporating the appropriate dose of a compound of Formula 1 with carriers according to the accepted pharmaceutical practices. The heterocyclic homoprostanoidal derivatives will be present in an amount sufficient to produce anti-prostaglandin activity. Preferably the dosage unit forms will contain the compounds of Formula 1 in an amount of from about 10 mg. to about 1000 mg., advantageously from about 100 mg. to about 500 mg. Most advantageously equal daily doses are administered one to four times daily to provide a daily dosage regimen of from about 10 mg. to about 4000 mg.

The pharmaceutical carrier employed may be, for example, either a solid or liquid. Exemplary of solid carriers are lactose, terra alba, talc, sucrose, gelatin, agar, pectin, acacia, magnesium stearate, stearic acid, and the like. Exemplary of liquid carriers are syrup, peanut oil, olive oil, water and the like. Similarly, the carrier as diluent can include any time delay material well known to the art such as glyceryl monostearate or glyceryl distearate alone or with a wax.

A wide variety of pharmaceutical forms can be employed. Thus if a solid carrier is used the preparation can be tableted, placed in a hard gelatin capsule in powder or pellet form or in the form of a troche or lozenge. The amount of solid carrier will vary widely but preferably will be about 25 mg. to about 1 g. If a liquid carrier is used, the preparation will be in the form of a syrup, emulsion, soft gelatin capsule, sterile injectable liquid such as an ampule, or an aqueous liquid suspension.

The following examples illustrate the preparation of specific compounds having antiprostaglandin activity. However, this should not be construed as a limitation of the invention since other variations will be obvious to those skilled in the art.

EXAMPLE 1

Threo-9,10-dihydroxystearic acid (31.4 g.) is dissolved in 500 ml. of methanol and heated under reflux with an acid catalyst, such as AG 50W-X8 resin, for approximately 12 hours. The mixture is filtered and the solvent removed under reduced pressure. The solid is recrystallized from hexane to yield methylthreo-9,10-dihydroxystearate having a melting point of 65°–69° C.

Methyl threo-9,10-dihydroxystearate (3.5 g.) is dissolved in 250 ml. of ether. The solution is cooled to 0° C. and 2.4 g. of thionyl chloride is added. The HCl is removed by bubbling nitrogen through the solution for two hours at 0° C. followed by the addition of 80 ml. of hexane. The mixture is filtered and the filtrate concentrated under reduced pressure to yield 8$\xi$-trans)-10-oxo-9,11-dioxa-10-thia-1a-homoprostan-1-oic acid, methyl ester as an oil.

EXAMPLE 2

Employing methyl erythro-9,10-dihydroxystearate in place of the threo isomer as a starting material and following the procedure set forth in Example 1 yields (8$\xi$-cis)-10-oxo-9,11-dioxa-10-thia-1a-homoprostan-1-oic acid, methyl ester as an oil.

EXAMPLE 3

Threo-9,10-dihydroxystearic acid, 6.4 g. and 3.6 g. of paraformaldehyde are dissolved in 60 ml. of orthophosphoric acid and the solution is heated at 100° C. for approximately 14 hours. The reaction mixture is cooled and extracted with ether. The ether extracts are combined and the solvent removed under reduced pressure.

The product (8ξ-trans)-9,11-dioxa-1a-homoprostan-1-oic acid is yielded as a viscous oil.

EXAMPLE 4

A solution of potassium methylxanthate 13.5 ml. is added to 3.7 g. of cis 9,10-epoxyoctadecanoic acid in 100 ml. of methanol. The mixture is allowed to stand at 25° C. for two weeks and then filtered. The filtrate is neutralized to pH of 7 and concentrated to an oil under reduced pressure. The oil is chromatographed and the fractions combined and concentrated. The residue is crystallized from ether in hexane to give (8ξ-trans)-10-thioxo-9,11-dithia-1a-homoprostan-1-oic acid having a melting point of 47°–50° C.

EXAMPLE 5

| Ingredients | Mg/capsule |
| --- | --- |
| (8ξ-trans)-10-thioxo-9,11-dithia-1a-homoprostan-1-oic acid | 500 mg. |
| Lactose, U.S.P. | 50 mg. |
| Starch, U.S.A. | 50 mg. |

All the ingredients are thoroughly mixed and placed in a hard gelatin capsule.

One capsule is taken three times a day.

What is claimed is:

1. A pharmaceutical composition in dosage unit form which inhibits prostaglandin synthesis and antagonizes diarrhea induced by prostaglandin $E_2$ comprising a chemical compound of the formula:

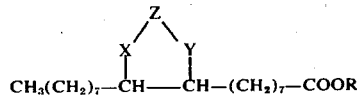

in which:

X and Y being the same are oxygen or sulfur;

Z is sulfoxide or methylene when X and Y are oxygen and thioxo when X and Y are sulfur; and R is hydrogen when Z is methylene or thioxo and lower alkyl when Z is sulfoxide and a pharmaceutical carrier.

2. The pharmaceutical composition of claim 1 in which both X and Y are oxygen and Z is sulfoxide.

3. The method of inhibiting prostaglandin synthesis and antagonizing diarrhea induced by prostaglandin $E_2$ which comprises administering internally to an animal chemical compound as defined in claim 1 in an amount sufficient to produce said activity.

4. The method of claim 3 in which both X and Y are oxygen and Z is sulfoxide.

5. A chemical compound of the formula:

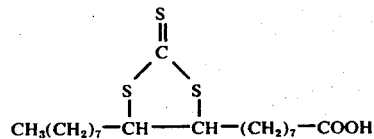

* * * * *